US011030276B2

(12) United States Patent
Wong

(10) Patent No.: US 11,030,276 B2
(45) Date of Patent: *Jun. 8, 2021

(54) METHODS AND APPARATUS FOR SORTING DATA

(71) Applicant: 10X Genomics, Inc., Pleasanton, CA (US)

(72) Inventor: Alexander Y. Wong, San Francisco, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 413 days.

This patent is subject to a terminal disclaimer.

(21) Appl. No.: 15/730,119

(22) Filed: Oct. 11, 2017

(65) Prior Publication Data

US 2018/0196781 A1  Jul. 12, 2018

Related U.S. Application Data

(63) Continuation of application No. 14/571,120, filed on Dec. 15, 2014, now Pat. No. 9,824,068.

(60) Provisional application No. 61/916,687, filed on Dec. 16, 2013.

(51) Int. Cl.
*G06F 17/18* (2006.01)
*G16B 30/00* (2019.01)

(52) U.S. Cl.
CPC ............. *G06F 17/18* (2013.01); *G16B 30/00* (2019.02)

(58) Field of Classification Search
CPC .................................. G06F 17/18; G16B 30/00
See application file for complete search history.

(56) References Cited

U.S. PATENT DOCUMENTS

| | | |
|---|---|---|
| 4,124,638 A | 11/1978 | Hansen |
| 5,185,099 A | 2/1993 | Delpuech et al. |
| 5,270,183 A | 12/1993 | Corbett et al. |
| 5,478,893 A | 12/1995 | Ghosh et al. |
| 5,756,334 A | 5/1998 | Perler et al. |
| 5,846,719 A | 12/1998 | Brenner et al. |
| 5,900,481 A | 5/1999 | Lough et al. |
| 5,942,609 A | 8/1999 | Hunkapiller et al. |
| 6,033,880 A | 3/2000 | Haff et al. |
| 6,057,149 A | 5/2000 | Burns et al. |
| 6,123,798 A | 9/2000 | Gandhi et al. |
| 6,171,850 B1 | 1/2001 | Nagle et al. |
| 6,172,218 B1 | 1/2001 | Brenner |

(Continued)

FOREIGN PATENT DOCUMENTS

| | | |
|---|---|---|
| EP | 1841879 A2 | 10/2007 |
| EP | 2635679 B1 | 4/2017 |

(Continued)

OTHER PUBLICATIONS

Margulies 2005 Supplementary methods (Year: 2005).
(Continued)

*Primary Examiner* — Huawen A Peng
(74) *Attorney, Agent, or Firm* — Wilson Sonsini Goodrich & Rosati

(57) ABSTRACT

A computer implemented system for genomic data sorting, comprising alignment and position mapping. The system maps each read to a position on the reference genome with which the read is associated, followed by sorting these reads by their mapped positions.

16 Claims, 4 Drawing Sheets

(56) References Cited

U.S. PATENT DOCUMENTS

| | | |
|---|---|---|
| 6,176,962 B1 | 1/2001 | Soane et al. |
| 6,297,006 B1 | 10/2001 | Drmanac et al. |
| 6,306,590 B1 | 10/2001 | Mehta et al. |
| 6,379,929 B1 | 4/2002 | Burns et al. |
| 6,409,832 B2 | 6/2002 | Weigl et al. |
| 6,492,118 B1 | 12/2002 | Abrams et al. |
| 6,632,606 B1 | 10/2003 | Ullman et al. |
| 6,915,679 B2 | 7/2005 | Chien et al. |
| 6,974,669 B2 | 12/2005 | Mirkin et al. |
| 7,294,503 B2 | 11/2007 | Quake et al. |
| 7,544,473 B2 | 6/2009 | Brenner |
| 7,622,076 B2 | 11/2009 | Davies et al. |
| 7,709,197 B2 | 5/2010 | Drmanac |
| 7,745,178 B2 | 6/2010 | Dong |
| 7,772,287 B2 | 8/2010 | Higuchi et al. |
| 7,901,891 B2 | 3/2011 | Drmanac |
| 7,910,354 B2 | 3/2011 | Drmanac et al. |
| 7,927,797 B2 | 4/2011 | Nobile et al. |
| 7,960,104 B2 | 6/2011 | Drmanac et al. |
| 7,972,778 B2 | 7/2011 | Brown et al. |
| 8,003,312 B2 | 8/2011 | Krutzik et al. |
| 8,053,192 B2 | 11/2011 | Bignell et al. |
| 8,067,159 B2 | 11/2011 | Brown et al. |
| 8,168,385 B2 | 5/2012 | Brenner |
| 8,298,767 B2 | 10/2012 | Brenner et al. |
| 8,318,433 B2 | 11/2012 | Brenner |
| 8,658,430 B2 | 2/2014 | Miller et al. |
| 8,835,358 B2 | 9/2014 | Fodor et al. |
| 8,975,302 B2 | 3/2015 | Light et al. |
| 9,012,370 B2 | 4/2015 | Hong |
| 9,012,390 B2 | 4/2015 | Holtze et al. |
| 9,029,085 B2 | 5/2015 | Agresti et al. |
| 9,085,798 B2 | 7/2015 | Chee |
| 9,089,844 B2 | 7/2015 | Hiddessen et al. |
| 9,126,160 B2 | 9/2015 | Ness et al. |
| 9,156,010 B2 | 10/2015 | Colston et al. |
| 9,194,861 B2 | 11/2015 | Hindson et al. |
| 9,216,392 B2 | 12/2015 | Hindson et al. |
| 9,238,206 B2 | 1/2016 | Rotem et al. |
| 9,266,104 B2 | 2/2016 | Link |
| 9,290,808 B2 | 3/2016 | Fodor et al. |
| 9,328,382 B2 | 5/2016 | Drmanac et al. |
| 9,417,190 B2 | 8/2016 | Hindson et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,701,998 B2 | 7/2017 | Hindson et al. |
| 9,764,322 B2 | 9/2017 | Hiddessen et al. |
| 9,824,068 B2 | 11/2017 | Wong et al. |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 1,001,187 A1 | 7/2018 | Belgrader et al. |
| 1,001,775 A1 | 7/2018 | Kaper et al. |
| 1,005,998 A1 | 8/2018 | Giresi et al. |
| 1,011,916 A1 | 11/2018 | Srinivasan et al. |
| 1,022,143 A1 | 3/2019 | Hardenbol et al. |
| 1,022,144 A1 | 3/2019 | Hindson et al. |
| 1,025,336 A1 | 4/2019 | Hindson et al. |
| 1,027,354 A1 | 4/2019 | Hindson et al. |
| 1,032,327 A1 | 6/2019 | Hindson et al. |
| 1,034,736 A1 | 7/2019 | Wong et al. |
| 1,035,777 A1 | 7/2019 | Bharadwaj et al. |
| 10,395,758 B2 | 8/2019 | Schnall-Levin |
| 1,040,028 A1 | 9/2019 | Hindson et al. |
| 1,042,832 A1 | 10/2019 | Belhocine et al. |
| 1,053,322 A1 | 1/2020 | Hindson et al. |
| 1,054,441 A1 | 1/2020 | Bharadwaj et al. |
| 1,054,927 A1 | 2/2020 | Bharadwaj et al. |
| 1,059,024 A1 | 3/2020 | Delaney et al. |
| 2001/0044109 A1 | 11/2001 | Mandecki |
| 2002/0005354 A1 | 1/2002 | Spence et al. |
| 2002/0034737 A1 | 3/2002 | Drmanac |
| 2002/0051971 A1 | 5/2002 | Stuelpnagel et al. |
| 2002/0119455 A1 | 8/2002 | Chan |
| 2002/0127736 A1 | 9/2002 | Chou et al. |
| 2003/0036206 A1 | 2/2003 | Chien et al. |
| 2003/0044836 A1 | 3/2003 | Levine et al. |
| 2003/0075446 A1 | 4/2003 | Culbertson et al. |
| 2003/0108897 A1 | 6/2003 | Drmanac |
| 2003/0124509 A1 | 7/2003 | Kenis et al. |
| 2003/0207260 A1 | 11/2003 | Trnovsky et al. |
| 2005/0221339 A1 | 10/2005 | Griffiths et al. |
| 2005/0250147 A1 | 11/2005 | MacEvicz |
| 2005/0266582 A1 | 12/2005 | Modlin et al. |
| 2006/0177832 A1 | 8/2006 | Brenner |
| 2006/0199193 A1 | 9/2006 | Koo et al. |
| 2006/0275782 A1 | 12/2006 | Gunderson et al. |
| 2007/0020640 A1 | 1/2007 | McCloskey et al. |
| 2007/0042419 A1 | 2/2007 | Barany et al. |
| 2007/0111241 A1 | 5/2007 | Cereb et al. |
| 2007/0172873 A1 | 7/2007 | Brenner et al. |
| 2007/0190543 A1 | 8/2007 | Livak |
| 2007/0196397 A1 | 8/2007 | Torii et al. |
| 2007/0207060 A1 | 9/2007 | Zou et al. |
| 2008/0056948 A1 | 3/2008 | Dale et al. |
| 2008/0166720 A1 | 7/2008 | Hsieh et al. |
| 2008/0241820 A1 | 10/2008 | Krutzik et al. |
| 2008/0242560 A1 | 10/2008 | Gunderson et al. |
| 2008/0268431 A1 | 10/2008 | Choy et al. |
| 2009/0005252 A1 | 1/2009 | Drmanac et al. |
| 2009/0011943 A1 | 1/2009 | Drmanac et al. |
| 2009/0047713 A1 | 2/2009 | Handique |
| 2009/0048124 A1 | 2/2009 | Leamon et al. |
| 2009/0099041 A1 | 4/2009 | Church et al. |
| 2009/0118488 A1 | 5/2009 | Drmanac et al. |
| 2009/0131543 A1 | 5/2009 | Weitz et al. |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155563 A1 | 6/2009 | Petsev et al. |
| 2009/0155781 A1 | 6/2009 | Drmanac et al. |
| 2009/0202984 A1 | 8/2009 | Cantor |
| 2009/0203531 A1 | 8/2009 | Kurn |
| 2009/0235990 A1 | 9/2009 | Beer |
| 2009/0264299 A1 | 10/2009 | Drmanac et al. |
| 2009/0269248 A1 | 10/2009 | Falb et al. |
| 2009/0286687 A1 | 11/2009 | Dressman et al. |
| 2010/0021973 A1 | 1/2010 | Makarov et al. |
| 2010/0022414 A1 | 1/2010 | Link et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105866 A1 | 4/2010 | Fraden et al. |
| 2010/0130369 A1 | 5/2010 | Shenderov et al. |
| 2010/0184928 A1 | 7/2010 | Kumacheva |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0033854 A1 | 2/2011 | Drmanac et al. |
| 2011/0091366 A1 | 4/2011 | Kendall et al. |
| 2011/0160078 A1 | 6/2011 | Fodor et al. |
| 2011/0257889 A1 | 10/2011 | Klammer et al. |
| 2011/0263457 A1 | 10/2011 | Krutzik et al. |
| 2011/0281738 A1 | 11/2011 | Drmanac et al. |
| 2011/0319281 A1 | 12/2011 | Drmanac |
| 2012/0015822 A1 | 1/2012 | Weitz et al. |
| 2012/0041727 A1 | 2/2012 | Mishra et al. |
| 2012/0071331 A1 | 3/2012 | Casbon et al. |
| 2012/0089339 A1* | 4/2012 | Ganeshalingam ...... G06F 16/22 702/19 |
| 2012/0135893 A1 | 5/2012 | Drmanac et al. |
| 2012/0184449 A1 | 7/2012 | Hixson et al. |
| 2012/0219947 A1 | 8/2012 | Yurkovetsky et al. |
| 2012/0230338 A1 | 9/2012 | Ganeshalingam et al. |
| 2012/0233202 A1* | 9/2012 | Ganeshalingam ...... G16B 30/00 707/769 |

(56) References Cited

U.S. PATENT DOCUMENTS

| | | |
|---|---|---|
| 2013/0130919 A1 | 5/2013 | Chen et al. |
| 2013/0157870 A1 | 6/2013 | Pushkarev et al. |
| 2013/0157899 A1 | 6/2013 | Adler, Jr. et al. |
| 2013/0185096 A1 | 7/2013 | Giusti et al. |
| 2013/0203605 A1 | 8/2013 | Shendure et al. |
| 2013/0246460 A1* | 9/2013 | Maltbie ............... G16B 20/00 707/771 |
| 2013/0268206 A1 | 10/2013 | Porreca et al. |
| 2013/0311106 A1 | 11/2013 | White et al. |
| 2013/0317755 A1 | 11/2013 | Mishra et al. |
| 2014/0200166 A1 | 7/2014 | Van et al. |
| 2014/0214334 A1 | 7/2014 | Plattner et al. |
| 2014/0221239 A1 | 8/2014 | Carman et al. |
| 2014/0227706 A1 | 8/2014 | Kato et al. |
| 2014/0272996 A1 | 9/2014 | Bemis |
| 2014/0274740 A1 | 9/2014 | Srinivasan et al. |
| 2014/0323316 A1 | 10/2014 | Drmanac et al. |
| 2014/0338753 A1 | 11/2014 | Sperling et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov |
| 2015/0066385 A1 | 3/2015 | Schnall-Levin et al. |
| 2015/0111256 A1 | 4/2015 | Church et al. |
| 2015/0133344 A1 | 5/2015 | Shendure et al. |
| 2015/0218633 A1 | 8/2015 | Hindson et al. |
| 2015/0220532 A1 | 8/2015 | Wong |
| 2015/0267191 A1 | 9/2015 | Steelman et al. |
| 2015/0298091 A1 | 10/2015 | Weitz et al. |
| 2015/0361418 A1 | 12/2015 | Reed |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |
| 2016/0024572 A1 | 1/2016 | Shishkin et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0122753 A1 | 5/2016 | Mikkelsen et al. |
| 2016/0122817 A1 | 5/2016 | Jarosz et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0281160 A1 | 9/2016 | Jarosz et al. |
| 2016/0289769 A1 | 10/2016 | Schwartz et al. |
| 2016/0304860 A1 | 10/2016 | Hindson et al. |
| 2016/0314242 A1 | 10/2016 | Schnall-Levin et al. |
| 2016/0348093 A1 | 12/2016 | Price et al. |
| 2016/0350478 A1 | 12/2016 | Chin et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0235876 A1 | 8/2017 | Jaffe et al. |
| 2017/0260584 A1 | 9/2017 | Zheng et al. |
| 2018/0030515 A1 | 2/2018 | Regev et al. |
| 2018/0071695 A1 | 3/2018 | Weitz et al. |
| 2018/0080075 A1 | 3/2018 | Brenner et al. |
| 2018/0105808 A1 | 4/2018 | Mikkelsen et al. |
| 2018/0265928 A1 | 9/2018 | Schnall-Levin et al. |
| 2018/0312822 A1 | 11/2018 | Lee et al. |
| 2018/0312873 A1 | 11/2018 | Zheng |
| 2018/0340169 A1 | 11/2018 | Belhocine et al. |
| 2018/0371545 A1 | 12/2018 | Wong et al. |
| 2019/0060890 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0085391 A1 | 3/2019 | Hindson et al. |
| 2019/0127731 A1 | 5/2019 | McDermott |
| 2019/0134633 A1 | 5/2019 | Bharadwaj et al. |
| 2019/0136316 A1 | 5/2019 | Hindson et al. |
| 2019/0153532 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0249226 A1 | 8/2019 | Bent et al. |
| 2019/0323088 A1 | 10/2019 | Boutet et al. |
| 2019/0345636 A1 | 11/2019 | McDermott et al. |
| 2019/0352717 A1 | 11/2019 | Schnall-Levin |
| 2019/0367997 A1 | 12/2019 | Bent et al. |
| 2019/0376118 A1 | 12/2019 | Belhocine et al. |
| 2020/0002763 A1 | 1/2020 | Belgrader et al. |
| 2020/0005902 A1 | 1/2020 | Mellen et al. |
| 2020/0032335 A1 | 1/2020 | Alvarado Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0105373 A1 | 4/2020 | Zheng |

FOREIGN PATENT DOCUMENTS

| | | |
|---|---|---|
| GB | 2097692 B | 5/1985 |
| JP | 2006507921 A | 3/2006 |
| JP | 2007193708 A | 8/2007 |
| JP | 2012525147 A | 10/2012 |
| WO | WO-84/02000 | 5/1984 |
| WO | WO-95/30782 | 11/1995 |
| WO | WO-9641011 A1 | 12/1996 |
| WO | WO-9909217 A1 | 2/1999 |
| WO | WO-99/52708 | 10/1999 |
| WO | WO-2000008212 A1 | 2/2000 |
| WO | WO-0026412 A1 | 5/2000 |
| WO | WO-2001002850 A1 | 1/2001 |
| WO | WO-0114589 A2 | 3/2001 |
| WO | WO-0190418 A1 | 11/2001 |
| WO | WO-0231203 A2 | 4/2002 |
| WO | WO-03096223 A1 | 11/2003 |
| WO | WO-2004010106 A2 | 1/2004 |
| WO | WO-2004065617 A2 | 8/2004 |
| WO | WO-2005040406 A1 | 5/2005 |
| WO | WO-2005049787 A2 | 6/2005 |
| WO | WO-2006030993 A1 | 3/2006 |
| WO | WO-2006040551 A2 | 4/2006 |
| WO | WO-2007081387 A1 | 7/2007 |
| WO | WO-2007139766 A2 | 12/2007 |
| WO | WO-2007147079 A2 | 12/2007 |
| WO | WO-2008134153 A1 | 11/2008 |
| WO | WO-2008150432 A1 | 12/2008 |
| WO | WO-2009015296 A1 | 1/2009 |
| WO | WO-2009023821 A1 | 2/2009 |
| WO | WO-2009085215 A1 | 7/2009 |
| WO | WO-2009152928 A2 | 12/2009 |
| WO | WO-2010004018 A2 | 1/2010 |
| WO | WO-2010033200 A2 | 3/2010 |
| WO | WO-2010104604 A1 | 9/2010 |
| WO | WO-2010115154 A1 | 10/2010 |
| WO | WO-2010117620 A2 | 10/2010 |
| WO | WO-2010127304 A2 | 11/2010 |
| WO | WO-2010148039 A2 | 12/2010 |
| WO | WO-2011028539 A1 | 3/2011 |
| WO | WO-2011066476 A1 | 6/2011 |
| WO | WO-2011074960 A1 | 6/2011 |
| WO | WO-2012048341 A1 | 4/2012 |
| WO | WO-2012055929 A1 | 5/2012 |
| WO | WO-2012061832 A1 | 5/2012 |
| WO | WO-2012100216 A2 | 7/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A2 | 8/2012 |
| WO | WO-2012142531 A2 | 10/2012 |
| WO | WO-2012142611 A2 | 10/2012 |
| WO | WO-2012149042 A2 | 11/2012 |
| WO | WO-2012166425 A2 | 12/2012 |
| WO | WO-2012167142 A2 | 12/2012 |
| WO | WO-2013019751 A1 | 2/2013 |

(56) References Cited

FOREIGN PATENT DOCUMENTS

| | | |
|---|---|---|
| WO | WO-2013035114 A1 | 3/2013 |
| WO | WO-2013036929 A1 | 3/2013 |
| WO | WO-2013055955 A1 | 4/2013 |
| WO | WO-2013096643 A1 | 6/2013 |
| WO | WO-2013123125 A1 | 8/2013 |
| WO | WO-2013126741 A1 | 8/2013 |
| WO | WO-2013177220 A1 | 11/2013 |
| WO | WO-2014028378 A2 | 2/2014 |
| WO | WO-2014028537 A1 | 2/2014 |
| WO | WO-2014093676 A1 | 6/2014 |
| WO | WO-2014108810 A2 | 7/2014 |
| WO | WO-2014132497 A1 | 9/2014 |
| WO | WO-2014165559 A2 | 10/2014 |
| WO | WO-2015015199 A2 | 2/2015 |
| WO | WO-2015044428 A1 | 4/2015 |
| WO | WO-2015164212 A1 | 10/2015 |
| WO | WO-2015200891 A1 | 12/2015 |
| WO | WO-2016040476 A1 | 3/2016 |
| WO | WO-2016061517 A2 | 4/2016 |
| WO | WO-2016126871 A2 | 8/2016 |
| WO | WO-2016130578 A1 | 8/2016 |
| WO | WO-2017015075 A1 | 1/2017 |
| WO | WO-2017197343 A2 | 11/2017 |
| WO | WO-2018039338 A1 | 3/2018 |
| WO | WO-2018119301 A1 | 6/2018 |
| WO | WO-2018119447 A2 | 6/2018 |
| WO | WO-2018172726 A1 | 9/2018 |
| WO | WO-2018191701 A1 | 10/2018 |
| WO | WO-2018213643 A1 | 11/2018 |
| WO | WO-2018226546 A1 | 12/2018 |
| WO | WO-2018236615 A1 | 12/2018 |
| WO | WO-2019028166 A1 | 2/2019 |
| WO | WO-2019040637 A1 | 2/2019 |
| WO | WO-2019083852 A1 | 5/2019 |
| WO | WO-2019084043 A1 | 5/2019 |
| WO | WO-2019084165 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020041148 A1 | 2/2020 |
| WO | WO-2020142779 A1 | 7/2020 |

OTHER PUBLICATIONS

Margulies et al. "Genome sequencing in microfabricated high-density picoliter reactors", Nature (2005) 437:376-380.

Aitman, et al. Copy number polymorphism in Fcgr3 predisposes to glomerulonephritis in rats and humans. Nature. Feb. 16, 2006;439(7078):851-5.

Balikova, et al. Autosomal-dominant microtia linked to five tandem copies of a copy-number-variable region at chromosome 4p16. Am J Hum Genet. Jan. 2008;82(1):181-7. doi: 10.1016/j.ajhg.2007.08.001.

Bansal et al. An MCMC algorithm for haplotype assembly from whole-genome sequence data,â€ (2008) Genome Res 18:1336-1346.

Bansal et al. "HapCUT: an efficient and accurate algorithm for the haplotype assembly problem," Bioinformatics (2008) 24:i153-i159.

Bedtools: General Usage,â€ http://bedtools.readthedocs.io/en/latest/content/generalusage.html; Retrieved from the Internet Jul. 8, 2016.

Braeckmans et al., Scanning the Code. Modern Drug Discovery. 2003:28-32.

Bray, "The JavaScript Object Notation (JSON) Data Interchange Format," Mar. 2014, retrieved from the Internet Feb. 15, 2015; https://tools.ietf.org/html/rfc7159.

Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.

Chen et al. BreakDancer: an algorithm for high-resolution mapping of genomic structural variation,â€ Nature Methods (2009) 6(9):677-681.

Choi, et al. Identification of novel isoforms of the EML4-ALK transforming gene in non-small cell lung cancer. Cancer Res. Jul. 1, 2008;68(13):4971-6. doi: 10.1158/0008-5472.CAN-07-6158.

Chokkalingam, et al. Probing cellular heterogeneity in cytokine-secreting immune cells using droplet-based microfluidics. Lab Chip. Dec. 21, 2013;13(24):4740-4. doi: 10.1039/c3lc50945a.

Cleary et al. Joint variant and de novo mutation identification on pedigrees from highthroughput sequencing data,â€ J Comput Biol (2014) 21:405-419.

Cook, et al. Copy-number variations associated with neuropsychiatric conditions. Nature. Oct. 16, 2008;455(7215):919-23. doi: 10.1038/nature07458.

Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun. 14, 2010:1059.

Fisher, et al. A scalable, fully automated process for construction of sequence-ready human exome targeted capture libraries. Genome Biol. 2011;12(1):R1. doi: 10.1186/gb-2011-12-1-r1. Epub Jan. 4, 2011.

Fulton et al., Advanced multiplexed analysis with the FlowMetrix system. Clin Chem. Sep. 1997;43(9): 1749-56.

Ghadessy, et al. Directed evolution of polymerase function by compartmentalized self-replication. Proc Natl Acad Sci U S A. Apr. 10, 2001;98(8):4552-7. Epub Mar. 27, 2001.

Gonzalez, et al. The influence of CCL3L1 gene-containing segmental duplications on HIV-1/Aids susceptibility. Science. Mar. 4, 2005;307(5714):1434-40. Epub Jan. 6, 2005.

Gordon et al. Consed: A Graphical Tool for Sequence Finishing,â€ Genome Research (1998) 8:198-202.

Heng et al. "Fast and accurate long-read alignment with Burrows-Wheeler transform," Bioinformatics (2010) 25(14): 1754-1760.

Huang et al. EagleView: A genome assembly viewer for next-generationsequencing technologies,â€ Genome Research (2008) 18:1538-1543.

Huebner, "Quantitative detection of protein expression in single cells using droplet microfluidics", Chem. Commun. 1218-1220 (2007).

Hug, et al. Measurement of the number of molecules of a single mRNA species in a complex mRNA preparation. J Theor Biol. Apr. 21, 2003;221(4):615-24.

Kanehisa et al. KEGG: Kyoto Encyclopedia of Genes and Genomes,â€ Nucleic Acids Research (2000) 28:27-30.

Khomiakova et al., Analysis of perfect and mismatched DNA duplexes by a generic hexanucleotide microchip. Mol Biol(Mosk). Jul.-Aug. 2003;37(4):726-41. Russian. Abstract only.

Kim et al. "HapEdit: an accuracy assessment viewer for haplotype assembly using massively parallel DNA-sequencing technologies," Nucleic Acids Research (2011) pp. 1-5.

Kirkness et al. Sequencing of isolated sperm cells for direct haplotyping of a human genome,â€ Genome Res (2013) 23:826-832.

Kitzman et al. "Haplotype-resolved genome sequencing of a Gujarati Indian individual." Nat Biotechnol (2011) 29:59-63.

Knight, et al. Subtle chromosomal rearrangements in children with unexplained mental retardation. Lancet. Nov. 13, 1999;354(9191):1676-81.

Layer et al. LUMPY: A probabilistic framework for structural variant discovery,â€ Genome Biology (2014) 15(6):R84.

Lippert et al. ""Algorithmic strategies for the single nucleotide polymorphism haplotype assembly problem,â€ Brief. Bionform (2002) 3:23-31.

Lo, et al. On the design of clone-based haplotyping. Genome Biol. 2013;14(9):R100.

(56) References Cited

OTHER PUBLICATIONS

Lupski. Genomic rearrangements and sporadic disease. Nat Genet. Jul. 2007;39(7 Suppl):S43-7.

Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.

Marcus. Gene method offers diagnostic hope. The Wall Street Journal. Jul. 11, 2012.

McKenna, Aaron et al. "The Genome Analysis Toolkit: A MapReduce Framework for Analyzing next-Generation DNA Sequencing Data." Genome Research 20.9 (2010): 1297-1303. PMC. Web. Feb. 2, 2017.

Miller et al. "Assembly Algorithms for next-generation sequencing data," Genomics, 95 (2010), pp. 315-327.

Mirzabekov, "DNA Sequencing by Hybridization—a Megasequencing Method and A Diagnostic Tool?" Trends in Biotechnology 12(1): 27-32 (1994).

Mouritzen et al., Single nucleotide polymorphism genotyping using locked nucleic acid (LNa). Expert Rev Mol Diagn. Jan. 2003;3(1):27-38.

Myllykangas et al. "Efficient targeted resequencing of human germline and cancer genomes by oligonucleotide-selective sequencing," Nat Biotechnol, (2011) 29:1024-1027.

Navin. The first five years of single-cell cancer genomics and beyond. Genome Res. Oct. 2015;25(10):1499-507. doi: 10.1101/gr.191098.115.

Peters, et al. Accurate whole-genome sequencing and haplotyping from 10 to 20 human cells. Nature. Jul. 11, 2012;487(7406):190-5. doi: 10.1038/Nature11236.

Pinto, et al. Functional impact of global rare copy number variation in autism spectrum disorders. Nature. Jul. 15, 2010;466(7304):368-72. doi: 10.1038/nature09146. Epub Jun. 9, 2010.

Pushkarev et al. Single-molecule sequencing of an individual human genome,â€ Nature Biotech (2009) 17:847-850.

Ropers. New perspectives for the elucidation of genetic disorders. Am J Hum Genet. Aug. 2007;81(2):199-207. Epub Jun. 29, 2007.

Schmitt, "Bead-based multiplex genotyping of human papillomaviruses", J. Clinical Microbial., 44:2 504-512 (2006).

Sebat, et al. Strong association of de novo copy number mutations with autism. Science. Apr. 20, 2007;316(5823):445-9. Epub Mar. 15, 2007.

Shendure et al. Accurate Multiplex Polony Sequencing of an Evolved bacterial Genome. Science (2005) 309:1728-1732.

Shlien, et al. Copy number variations and cancer. Genome Med. Jun. 16, 2009;1(6):62. doi: 10.1186/gm62.

Shlien, et al. Excessive genomic DNA copy number variation in the Li-Fraumeni cancer predisposition syndrome. Proc Natl Acad Sci U S A. Aug. 12, 2008;105(32):11264-9. doi: 10.1073/pnas.0802970105. Epub Aug. 6, 2008.

Simeonov et al., Single nucleotide polymorphism genotyping using short, fluorescently labeled locked nucleic acid (LNA) probes and fluorescence polarization detection. Nucleic Acids Res. Sep. 1, 2002;30(17):e91.

Sorokin et al., Discrimination between perfect and mismatched duplexes with oligonucleotide gel microchips: role of thermodynamic and kinetic effects during hybridization. J Biomol Struct Dyn. Jun. 2005;22(6):725-34.

SSH Tunnel—Local and Remote Port Forwarding Explained With Examples,â€ Trackets Blog, http://blog.trackets.com/2014/05/17/ssh-tunnel-local-and-remote-port-forwarding-explained-with-examples.html; Retrieved from the Internet Jul. 7, 2016.

Tewhey, et al. Microdroplet-based PCR amplification for large-scale targeted sequencing. Nat Biotechnol. Nov. 2009;27(11):1025-31. doi: 10.1038/nbt.1583. Epub Nov. 1, 2009.

The SAM/BAM Format Specificatio Working Group, "Sequence Allignment/ Map Format Specification," Dec. 28, 2014.

Wang, et al. Digital karyotyping. Proc Natl Acad Sci U S A. Dec. 10, 2002;99(25):16156-61. Epub Dec. 2, 2002.

Wang et al., Single nucleotide polymorphism discrimination assisted by improved base stacking hybridization using oligonucleotide microarrays. Biotechniques. 2003;35:300-08.

Weaver, "Rapid clonal growth measurements at the single-cell level: gel microdroplets and flow cytometry", Biotechnology, 9:873-877 (1991).

Wheeler et al., "Database resources of the National Center for Biotechnology Information," Nucleic Acids Res. (2007) 35 (Database issue): D5-12.

Zerbino, Daniel, "Velvet Manual—version 1.1," Aug. 15, 2008, pp. 1-22.

Zerbino et al. "Velvet: Algorithms for de novo short read assembly using de Bruijn graphs," Genome Research (2008) 18:821-829.

Zheng, X.Y. et al. "Haplotyping germline and cancer genomes with high-throughput linked-read sequencing" Nature Biotech (Feb. 1, 2016) 34(3):303-311.

Zong, et al. Genome-wide detection of single-nucleotide and copy-number variations of a single human cell. Science. Dec. 21, 2012;338(6114):1622-6. doi: 10.1126/science.1229164.

Zheng, X. SeqArray: an R/Bioconductor Package for Big Data Management of Genome-Wide Sequencing Variants, Department of Biostatistics; University of Washington-Seattle; Dec. 28, 2014.

Co-pending U.S. Appl. No. 16/428,656, filed May 31, 2019.

Jarosz, M. et al. "Using 1 ng of DNA to detect haplotype phasing and gene fusions from whole exome sequencing of cancer cell lines" Cancer Res (2015) 75(suppl5):4742.

McCoy, R. et al. "Illumina TruSeq Synthetic Long-Reads Empower De Novo Assembly and Resolve Complex, Highly-Repetitive Transposable Elements" PLOS (2014) 9(9):e1016689.

Ritz, A. et al. "Characterization of structural variants with single molecule and hybrid sequencing approaches" Bioinformatics (2014) 30(24):3458-3466.

Ekblom, R. et al. "A field guide to whole-genome sequencing, assembly and annotation" Evolutionary Apps (Jun. 24, 2014) 7(9):1026-1042.

Voskoboynik, A. et al. The genome sequence of the colonial chordate, Botryllus schlosseri. eLife, 2:e00569 (2013). doi: 10.7554/eLife.00569. Epub Jul. 2, 2013.

Zerbino, D.R. "Using the Velvet de novo assembler for short-read sequencing technologies" Curr Protoc Bioinformatics. Sep. 2010;Chapter 11:Unit 11.5. doi: 10.1002/0471250953.bi1105s31.

Co-pending U.S. Appl. No. 15/985,388, filed May 21, 2018.

10X Genomics, Inc. CG000153 Rev A. Chromium Single Cell DNA Reagent Kits User Guide. 2018.

10X Genomics, Inc. CG000184 Rev A. Chromium Single Cell 3' Reagent Kits v3 User Guide with Feature Barcoding Technology for CRISPR Screening. 2018.

10X Genomics, Inc. CG000185 Rev B. Chromium Single Cell 3' Reagent Kits User Guide with Feature Barcoding Technology for Cell Surface Protein. 2018.

10X Genomics, Inc. CG000208 Rev E. Chromium Next GEM Single Cell V(D)J reagent Kits v1.1 User Guide with Feature Barcode Technology for Cell Surface Protein. 2020.

10X Genomics, Inc. CG000209 Rev D. Chromium Next GEM Single Cell ATAC Reagent Kits v1.1 User Guide. 2020.

10X Genomics, Inc. CG000239 Rev B. Visium Spatial Gene Expression Reagent Kits User Guide. 2020.

10X Genomics, Inc. CG00026. Chromium Single Cell 3' Reagent Kit User Guide. 2016.

10X Genomics, Inc. LIT00003 Rev B Chromium Genome Solution Application Note. 2017.

Abate, A.R. et al. "Beating Poisson encapsulation statistics using close-packed ordering" Lab on a Chip (Sep. 21, 2009) 9(18):2628-2631.

Adamson, et al., "Production of arrays of chemically distinct nanolitre plugs via repeated splitting in microfluidic devices", Lab Chip 6(9): 1178-1186 (Sep. 2006).

Agasti, S.S. et al. "Photocleavable DNA barcode-antibody conjugates allow sensitive and multiplexed protein analysis in single cell" J Am Chem Soc (2012) 134(45):18499-18502.

Altemos, et al., "Genomic Characterization of Large Heterochromatic Gaps in the Human Genome Assembly," PLOS Computational Biology, May 15, 2014, vol. 10, Issue 5, 14 pages.

(56) References Cited

OTHER PUBLICATIONS

Amini, S. et al. "Haplotype-resolved whole-genome sequencing by contiguity-preserving transposition and combinatorial indexing" Nature Genetics (2014) 46:1343-1349 doi:10.1038/ng.3119.
Baret, "Surfactants in droplet-based microfluidics" Lab Chip (12(3):422-433 (2012).
Beer, et al. On-Chip, Real-Time, Single-Copy Polymerase Chain Reaction in Picoliter Droplets. Anal Chem 79:8471-8475 (2007).
Brenner, et al. "In vitro cloning of complex mixtures of DNA on microbeads: physical separation of differentially expressed cDNAs." Proc Natl Acad Sci U S A. Feb. 15, 2000;97(4):1665-70.
Browning, et al. Haplotype phasing: existing methods and new developments. Nat Rev Genet. Sep. 16, 2011;12(10):703-14. doi: 10.1038/nrg3054. Review.
Buchman GW, et al. Selective RNA amplification: a novel method using dUMP-containing primers and uracil DNA glycosylase. PCR Methods Appl. Aug. 1993; 3(1):28-31.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-15. Epub Aug. 9, 2001.
Chien et al. "Multiport flow-control system for lab-on-a-chip microfluidic devices", Fresenius J. Anal Chem, 371:106-111 (Jul. 27, 2001).
Co-pending U.S. Appl. No. 16/434,076, filed Jun. 6, 2019.
Co-pending U.S. Appl. No. 16/434,084, filed Jun. 6, 2019.
Co-pending U.S. Appl. No. 16/434,102, filed Jun. 6, 2019.
Co-pending U.S. Appl. No. 16/530,930, filed Aug. 2, 2019.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Depristo, et al. A framework for variation discovery and genotyping using next-generation DNA sequencing data. Nature Genet 43:491-498 (2011).
Duffy et al., Rapid Protyping of Microfluidic Systems and Polydimethylsiloxane, Anal Chem 70:4974-4984 (1998).
Gericke, et al. Functional cellulose beads: preparation, characterization, and applications. Chemical reviews 113.7 (2013): 4812-4836.
Hiatt, et al. Parallel, tag-directed assembly of locally derived short sequence reads. Nat Methods. Feb. 2010;7(2):119-22. Epub Jan. 17, 2010.
Islam, et al. Highly multiplexed and strand-specific single-cell RNA 5' end sequencing. Nat Protoc. Apr. 5, 2012;7(5):813-28. doi: 10.1038/nprot.2012.022.
Jaitin, et al. Massively parallel single-cell RNA-seq for marker-free decomposition of tissues into cell types. Science. Feb. 14, 2014;343(6172):776-9. doi: 10.1126/science.1247651.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Kenis, et al. Microfabrication Inside Capillaries Using Multiphase Laminar Flow Patterning. Science. 1999; 285:83-85.
Kivioja, et al. Counting absolute numbers of molecules using unique molecular identifiers. Nat Methods. Nov. 20, 2011;9(1):72-4.
Klein, et al. Droplet barcoding for single-cell transcriptomics applied to embryonic stem cells. Cell. May 21, 2015; 161:1187-1201.
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip The Royal Soc. of Chem. 8: 1110-1115 (2008).

Lagally, et al. Single-Molecular DNA Amplification and Analysis in an Integrated Microfluidic Device. Anal Chem. Feb. 1, 2001;73(3):565-70.
Lennon et al. A scalable, fully automated process for construction of sequence-ready barcoded libraries for 454. Genome Biology 11:R15 (2010).
Madl, et al. "Bioorthogonal Strategies for Engineering Extracellular matrices", Madal, Chritopher, Adv. Funct. Master. Jan. 19, 2018, vol. 28, 1706046, pp. 1-21.
Nisisako, et al. Droplet formation in a microchannel network. Lab Chip. Feb. 2002;2(1):24-6. Epub Jan. 18, 2002.
Nisisako, T. et al. Droplet Formation in a Microchannel on PMMA Plate. Micro Total Analysis Systems. 2001. Kluwer Academic Publishers. pp. 137-138.
Nisisako, T. et al., Microfluidics large-scale integration on a chip for mass production of monodisperse droplets and particles, The Royal Society of Chemistry: Lab Chip, (Nov. 23, 2007) 8:287-293.
Novak, R. et al., "Single cell multiplex gene detection and sequencing using microfluidicallygenerated agarose emulsions" Angew. Chem. Int. Ed. Engl. (2011) 50(2):390-395.
Orakdogen, N. "Novel responsive poly(N,N-dimethylaminoethyl methacrylate) gel beads: preparation, mechanical properties and pH-dependent swelling behavior" J Polym Res (2012) 19:9914.
Perrott, Jimmy. Optimization and Improvement of Emulsion PCR for the Ion Torrent Next-Generation Sequencing Platform. (2011) Thesis.
Priest, et al. Generation of Monodisperse Gel Emulsions in a Microfluidic Device, Applied Physics Letters, 88:024106 (2006).
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-11. URL:http://454.com/downloads/my454/documentation/technical-bulletins/TCB-09004 Using MultiplexIdentifierAdaptorsForTheGSFLXTitaniumSeriesChemistry-BasicMIDSet.pdf.
Rotem, A. et al., "High-throughput single-cell labeling (Hi-SCL) for RNA-Seq using drop-based microfluidics" PLOS One (May 22, 2015) 0116328 (14 pages).
Saikia, et al. Simultaneous multiplexed amplicon sequencing and transcriptome profiling in single cells. Nat Methods. Jan. 2019;16(1):59-62. doi: 10.1038/s41592-018-0259-9. Epub Dec. 17, 2018.
Schubert, et al. Microemulsifying fluorinated oils with mixtures of fluorinated and hydrogenated surfactants. Colloids and Surfaces A; Physicochemical and Engineering Aspects, 84(1994) 97-106.
Seiffert, et al. Microfluidic fabrication of smart microgels from macromolecular precursors.Polymer. vol. 51, Issue 25, Nov. 26, 2010, pp. 5883-5889.
Seiffert, S. et al., "Smart microgel capsules from macromolecular precursors" J. Am. Chem. Soc. (2010) 132:6606-6609.
Shah, et al. "Fabrication of mono disperse thermosensitive microgels and gel capsules in micro fluidic devices", Soft Matter, 4:2303-2309 (2008).
Smith, et al. Highly-multiplexed barcode sequencing: an efficient method for parallel analysis of pooled samples. Nucleic Acids Research, 38(13): e142 (2010).
Song, et al. Reactions in droplets in microfluidic channels. Angew Chem Int Ed Engl. Nov. 13, 2006;45(44):7336-56.
Thaxton, C.S. et al. "A Bio-Bar-Code Assay Based Upon Dithiothreitol Oligonucleotide Release" Anal Chem (2005) 77:8174-8178.
Thorsen, et al. Dynamic pattern formation in a vesicle-generating microfluidic device. Physical Review Letters. American Physical Society. 2001; 86(18):4163-4166.
Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.

(56) References Cited

OTHER PUBLICATIONS

Uttamapinant, et al. Fast, cell-compatible click chemistry with copper-chelating azides for biomolecular labeling. Angew. Chem. Int. End. Engl., Jun. 11, 2012: 51(24) pp. 5852-5856.
Weigl, et al. Microfluidic Diffusion-Based Separation and Detection. Science. 1999; pp. 346-347.
Zhang, et al. One-step fabrication of supramolecular microcapsules from microfluidic droplets. Science. Feb. 10, 2012;335(6069):690-4. doi: 10.1126/science.1215416.
Zhang, et al. Reconstruction of DNA sequencing by hybridization. Bioinformatics. Jan. 2003;19(1):14-21.
Zheng, et al. Massively parallel digital transcriptional profiling of single cells. Nat Commun. Jan. 16, 2017;8:14049. doi: 10.1038/ncomms14049.
Zhu, et al. Reverse transcriptase template switching: a SMART approach for full-length cDNA library construction. Biotechniques. Apr. 2001;30(4):892-7.
Co-pending U.S. Appl. No. US16/708,214, filed Dec. 9, 2019.
Co-pending U.S. Appl. No. US16/737,762, filed Jan. 8, 2020.
Co-pending U.S. Appl. No. US16/737,770, filed Jan. 8, 2020.
Co-pending U.S. Appl. No. US16/789,273, filed Feb. 12, 2020.
Co-pending U.S. Appl. No. US16/789,287, filed Feb. 12, 2020.
Co-pending U.S. Appl. No. US16/800,450, filed Feb. 25, 2020.
Co-pending U.S. Appl. No. US16/814,908, filed Mar. 10, 2020.
PCT/US2020/017785 Application filed on Feb. 11, 2020 by Ziraldo, Solongo B. et al. 0.
PCT/US2020/017789 Application filed on Feb. 11, 2020 by Belhocine, Zahara Kamila et al. 0.

\* cited by examiner

METHODS AND APPARATUS FOR SORTING DATA

CROSS-REFERENCE

This application is a Continuation Application of U.S. application Ser. No. 14/571,120, filed Dec. 15, 2014, which claims the benefit of U.S. Provisional Patent Application No. 61/916,687, filed Dec. 16, 2013, each of which is incorporated herein by reference in its entirety for all purposes.

TECHNICAL FIELD

The present disclosure generally relates to sorting data. The disclosure relates more specifically to improving efficiency of sorting data where the sort function is non-injective with a linearly ordered, finite codomain.

BACKGROUND

The approaches described in this section could be pursued, but are not necessarily approaches that have been previously conceived or pursued. Therefore, unless otherwise indicated herein, the approaches described in this section are not prior art to the claims in this application and are not admitted to be prior art by inclusion in this section.

Current state-of-the-art genome sequencing machines do not, as one might expect, produce one continuous output sequence of the entire genome. Rather, they generate large numbers of relatively short fragments of sequence called reads, which range from dozens to thousands of base pairs in length. Because these reads are output by the machine in no particular order, the first step in analyzing the data in prior approaches is typically to map each read to a position on the reference genome with which the read is associated. This is called alignment. The second step in prior approaches is typically to sort these reads by their mapped positions. Genome sequencing produces large quantities of data that can take hours or days to align and sort, so prior approaches can be improved by eliminating or making more efficient the steps in this analysis.

SUMMARY

The appended claims may serve as a summary of the disclosure.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The foregoing needs, and other needs and objectives that will become apparent from the following description, are achieved in the present invention, which comprises in one embodiment a method and apparatus for sorting data. Based on the foregoing, there is a clear need for improved ways to sort data.

The present approach improves sorting efficiency by eliminating the sorting step and producing a sorted result directly from the alignment step.

While the present disclosure is motivated by the problem of genome sequence data analysis, it can be applied to any problem with the same general characteristics. The genome sequencing problem can be generalized as follows:

Consider the human genome which comprises roughly 3 billion base pairs. If L is the actual length, then the genome can be represented as a string H of length L over a finite alphabet $\{A,C,T,G\}$. Reads can then be generalized as the set of all strings over the same alphabet with any length from 1 to L inclusive. The process of mapping a read to a position on the genome is therefore a function whose domain is all possible read strings and whose codomain is positions on the reference genome, which is the linearly ordered, finite set $\{1 \ldots L\}$. As reads of different lengths can be mapped to the same position, this function is non-injective. The present disclosure is therefore applicable to any problem that is equivalent to sorting elements from a finite set where the ordering function is non-injective to a codomain that is a linearly ordered, finite set.

Structural Overview of Data Sorting System

Figure 1A:
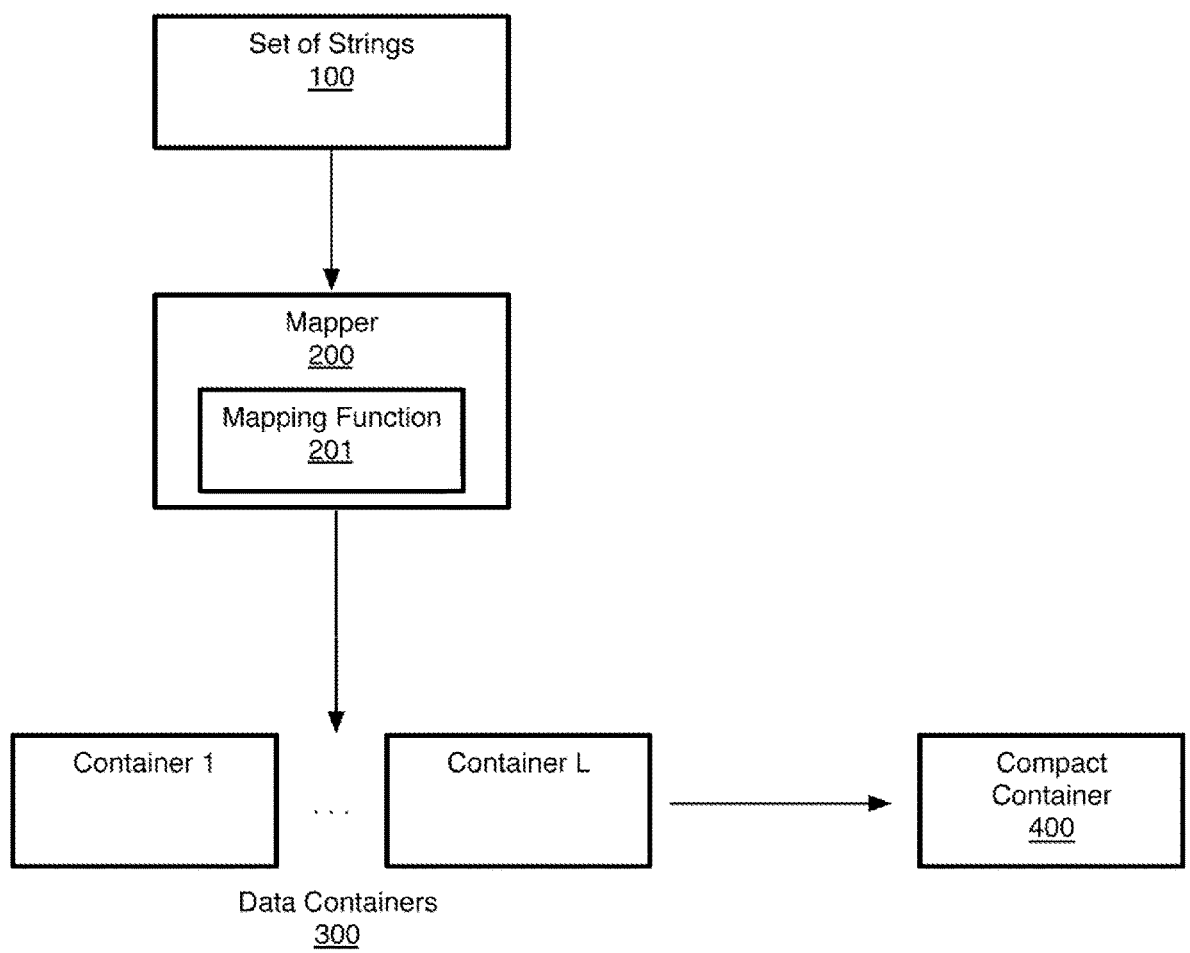
FIG. 1A illustrates a block diagram providing a high-level view of an example data processing system that may be used in an approach for sorting data.

FIG. 1A is a block diagram providing a high-level view of an example data processing system that may be used in an approach for sorting data. In one embodiment, there is initially a set of strings 100 of various lengths ranging from 1 to L, over a given finite alphabet. In various embodiments, strings 100 may be stored in computer storage devices of different types such as volatile main memory, non-volatile storage such as disk or FLASH memory, or other digital electronic storage. There can also be a processing element called the mapper 200, which may be implemented in various embodiments using digital logic in a special-purpose computer, or using one or more computer programs or other software elements that are executed using a general-purpose computer. The mapper 200 can be configured, given the set of strings 100 as input, to apply a non-injective mapping function 201 to each input string and to output each string paired with a position value, which can be a member of the codomain of the mapping function 201.

The embodiment can also include a set of data storage containers 300. The number of storage containers 300 may be equal to L, the number of elements in the codomain of the mapping function. Each of the storage containers 300 is addressable by one of the elements in the codomain. In the example of genome sequencing, there would be roughly 3 billion storage containers 300, one for each base pair, and each of the storage containers is addressable by the position in the genome that it represents.

Optionally one or more compact containers 400 may be provided. The function of compact containers 400 is further described in other sections.

The mapper 200 may be configured to both address any individual one of the storage containers 300 and to add a new data element to that container in O(1) time, constant in the number of containers n. One suitable implementation is an in-memory array of linked lists where each of the storage containers 300 is a linked list and the array is indexed by genome position. Another suitable implementation is a set of on-disk files whose filenames are genome positions and which can each have data appended to it in constant time.

Figure 1B:
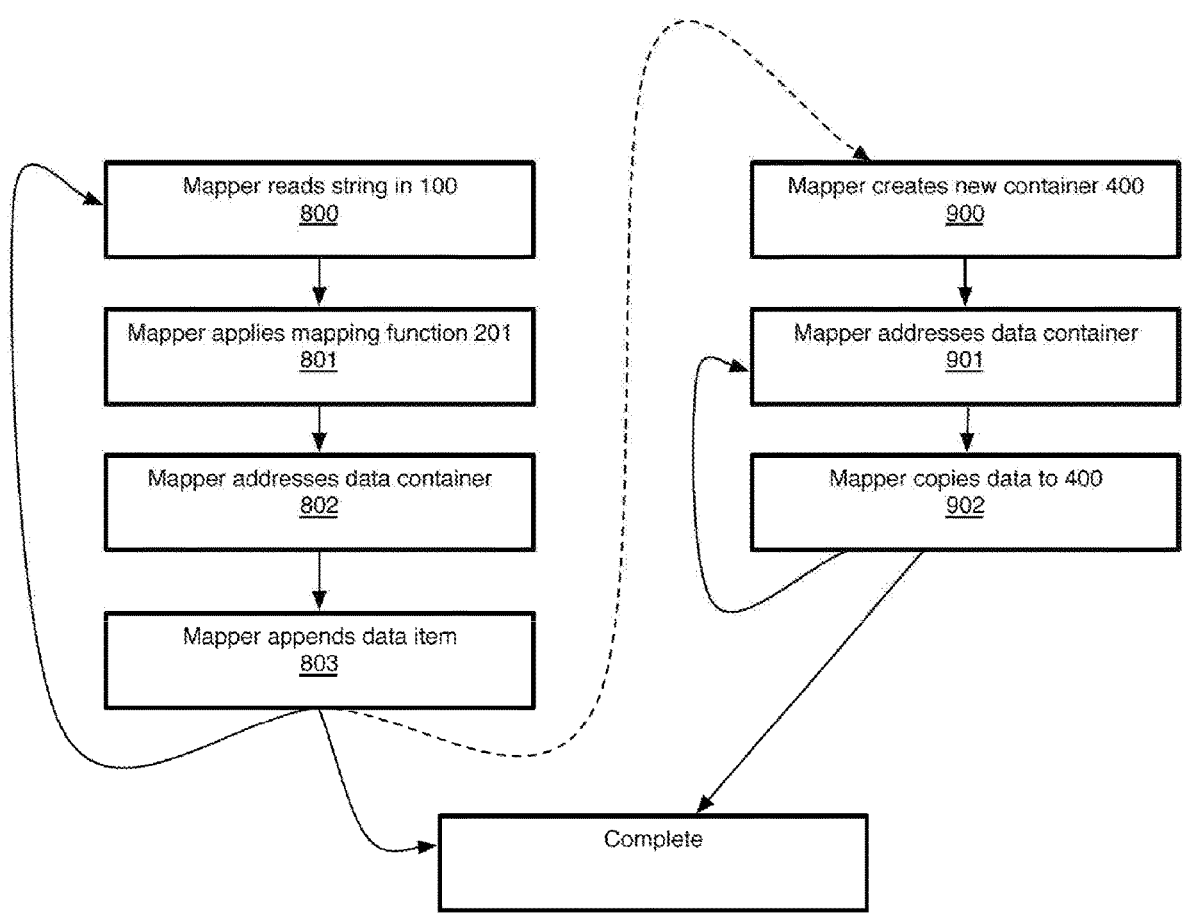
FIG. 1B illustrates a flow diagram where one example method of processing implements the example system of FIG. 1A.

FIG. 1B is a flow diagram that illustrates one method of processing using the example system of FIG. 1A. In an embodiment, the process of FIG. 1B may be implemented using mapper 200.

In step 800, the mapper 200 can read a particular one of the strings in the set 100.

In step 801, the mapper can apply the mapping function 201 to the particular string, which yields a position value for that string.

In step 802, the mapper can address the data container associated with the position value that was determined at step 801.

In step 803, the mapper cam append the particular string and its position value to the data container that was addressed at step 802. Step 803 may include forming a data item that includes the particular string and its position value prior to performing the appending. Data containers may contain more than one data item when multiple strings map to the same position value.

The mapper 200 can then loop back to step 800 until all strings in the set 100 have been processed. For some applications, the output as stored in the data containers 300 at this point can be sufficient as a final result. The data are already sorted and can be accessed in a linear ordered fashion by simply traversing the containers in order. No separate sorting step is required.

Compact Output

If the strings in set 100 are non-unique or there are fewer than L strings, then some of the data containers 300 may not contain any data items. In this situation, the final output can be made more compact, for example, by adding the following steps:

In step 900, the mapper 200 creates a new compact data container 400.

In step 901, the mapper addresses the first of the original data containers 300.

In step 902, the mapper copies any data items found in the first container addressed at step 901, and appends the data items to the new data container 400.

The mapper then loops back to step 901 and addresses the next one of the original data containers 300, and repeats this process until all of the original data containers have been copied and appended to the new compact data container 400.

This operation is O(n) linear in the number of strings in 100.

Non-Deterministic Mapping Function

In some applications the mapping function can map a string to multiple values in the codomain, each with a probability or score associated with it. Such a non-deterministic mapping function can be accommodated by altering step 803 to append the string, the position value, and the probability or score, to each of the data containers to which the mapping function maps the string. All other aspects of the processing can remain the same and the advantages of the present approach are preserved.

Hardware Overview

According to one embodiment, the techniques described herein can be implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 2:
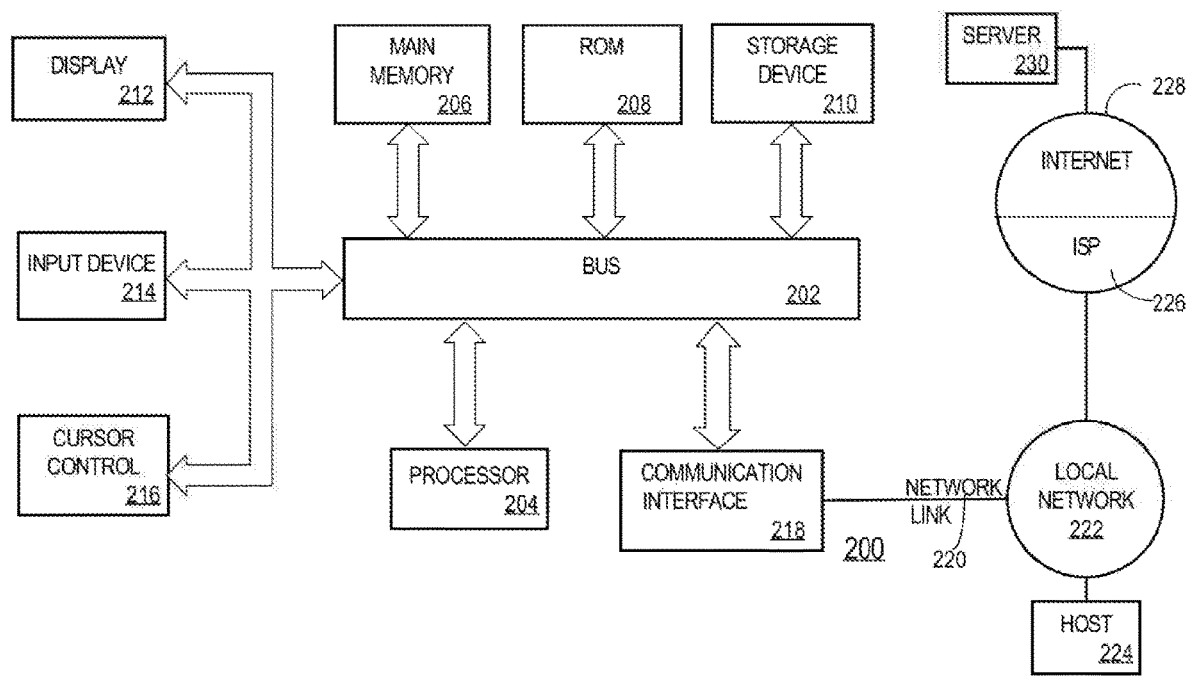
FIG. 2 illustrates a block diagram where a computer system implements an example sorting algorithm described herein.

For example, FIG. 2 is a block diagram that illustrates a computer system 200 upon which an embodiment of the invention may be implemented. Computer system 200 can include a bus 202 or other communication mechanism for communicating information, and a hardware processor 204 coupled with bus 202 for processing information. Hardware processor 204 may be, for example, a general purpose microprocessor.

Computer system 200 can also include a main memory 206, such as a random access memory (RAM) or other dynamic storage device, coupled to bus 202 for storing information and instructions to be executed by processor 204. Main memory 206 also may be used for storing temporary variables or other intermediate information during execution of instructions to be executed by processor 204. Such instructions, when stored in non-transitory storage media accessible to processor 204, can render computer system 200 into a special-purpose machine that is customized to perform the operations specified in the instructions.

Computer system 200 can further include a read only memory (ROM) 208 or other static storage device coupled to bus 202 for storing static information and instructions for processor 204. A storage device 210, such as a magnetic disk or optical disk, can be provided and coupled to bus 202 for storing information and instructions.

Computer system 200 may be coupled via bus 202 to a display 212, such as a cathode ray tube (CRT), for displaying information to a computer user. An input device 214, including alphanumeric and other keys, can be coupled to bus 202 for communicating information and command selections to processor 204. Another type of user input device is cursor control 216, such as a mouse, a trackball, or cursor direction keys for communicating direction information and command selections to processor 204 and for controlling cursor movement on display 212. This input device typically can have two degrees of freedom in two axes, a first axis (e.g., x) and a second axis (e.g., y), that can allow the device to specify positions in a plane.

Computer system 200 may implement the techniques described herein using customized hard-wired logic, one or more ASICs or FPGAs, firmware and/or program logic which in combination with the computer system causes or programs computer system 200 to be a special-purpose machine. According to one embodiment, the techniques herein can be performed by computer system 200 in response to processor 204 executing one or more sequences of one or more instructions contained in main memory 206. Such instructions may be read into main memory 206 from another storage medium, such as storage device 210. Execution of the sequences of instructions contained in main memory 206 can cause processor 204 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage device 210. Volatile media includes dynamic memory, such as main memory 206. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media can participate in transferring information between storage media. For example, transmission media can include coaxial cables, copper wire and fiber optics, including the wires that comprise bus 202. Transmission media can also take the form of acoustic or light waves, such as those generated during radio-wave and infra-red data communications.

Various forms of media may be involved in carrying one or more sequences of one or more instructions to processor 204 for execution. For example, the instructions may initially be carried on a magnetic disk or solid state drive of a remote computer. The remote computer can load the instructions into its dynamic memory and send the instructions over a telephone line using a modem. A modem local to computer system 200 can receive the data on the telephone line and use an infra-red transmitter to convert the data to an infra-red signal. An infra-red detector can receive the data carried in the infra-red signal and appropriate circuitry can place the data on bus 202. Bus 202 can carry the data to main memory 206, from which processor 204 can retrieve and execute the instructions. The instructions received by main memory 206 may optionally be stored on storage device 210 either before or after execution by processor 204.

Computer system 200 can also include a communication interface 218 coupled to bus 202. Communication interface 218 can provide a two-way data communication coupling to a network link 220 that is connected to a local network 222. For example, communication interface 218 may be an integrated services digital network (ISDN) card, cable modem, satellite modem, or a modem to provide a data communication connection to a corresponding type of telephone line. As another example, communication interface 218 may be a local area network (LAN) card to provide a data communication connection to a compatible LAN. Wireless links may also be implemented. In any such implementation, communication interface 218 can send and receive electrical, electromagnetic or optical signals that carry digital data streams representing various types of information.

Network link 220 typically can provide data communication through one or more networks to other data devices. For example, network link 220 may provide a connection through local network 222 to a host computer 224 or to data equipment operated by an Internet Service Provider (ISP) 226. ISP 226 in turn can provide data communication services through the world wide packet data communication network now commonly referred to as the "Internet" 228. Local network 222 and Internet 228 can both use electrical, electromagnetic or optical signals that carry digital data streams. The signals through the various networks and the signals on network link 220 and through communication interface 218, which carry the digital data to and from computer system 200, are example forms of transmission media.

Computer system 200 can send messages and receive data, including program code, through the network(s), network link 220 and communication interface 218. In the Internet example, a server 230 might transmit a requested code for an application program through Internet 228, ISP 226, local network 222 and communication interface 218.

The received code may be executed by processor 204 as it is received, and/or stored in storage device 210, or other non-volatile storage for later execution.

Benefits of Certain Embodiments

In an embodiment, a solution as described herein can yield a number of benefits compared to prior solutions:

Prior approaches to aligning and sorting genome sequence reads can require a separate sort step which runs in O(n log n), or perhaps O(n log log n) time at best. The present approach improves efficiency by eliminating an explicit sort step. For some applications, no additional computation or processing is required after alignment. If a more compact output is desired, this can be accomplished with an additional linear O(n) step, which is still faster than a full sort.

Control Systems

Figure 3:
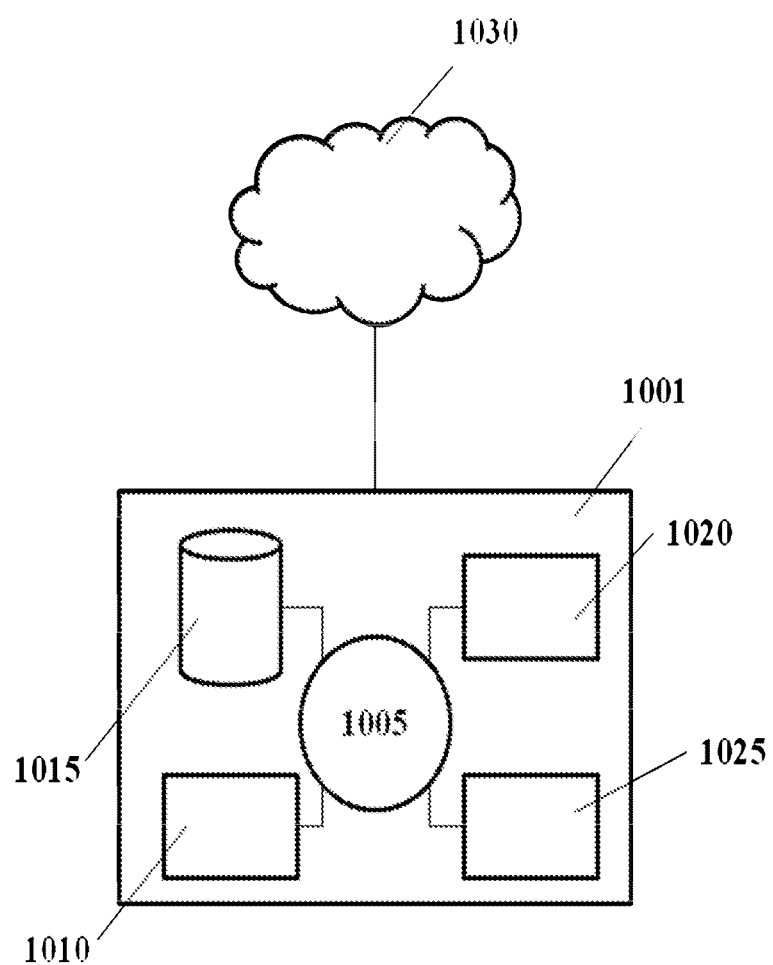
FIG. 3 illustrates an example computing architecture for implementing the subject matter described herein.

The present disclosure provides computer control systems that are programmed to implement methods of the disclosure. FIG. 3 shows an example computer system 1001 that is programmed or otherwise configured to sort data. The computer system 1001 can regulate various aspects of data sorting of the present disclosure, such as, for example, data alignment, mapping, networking.

The computer system 1001 includes a central processing unit (CPU, also "processor" and "computer processor" herein) 1005, which can be a single core or multi core processor, or a plurality of processors for parallel processing. The computer system 1001 also includes memory or memory location 1010 (e.g., random-access memory, read-only memory, flash memory), electronic storage unit 1015 (e.g., hard disk), communication interface 1020 (e.g., network adapter) for communicating with one or more other systems, and peripheral devices 1025, such as cache, other memory, data storage and/or electronic display adapters. The memory 1010, storage unit 1015, interface 1020 and peripheral devices 1025 are in communication with the CPU 1005 through a communication bus (solid lines), such as a motherboard. The storage unit 1015 can be a data storage unit (or data repository) for storing data. The computer system 1001 can be operatively coupled to a computer network ("network") 1030 with the aid of the communication interface 1020. The network 1030 can be the Internet, an internet and/or extranet, or an intranet and/or extranet that is in communication with the Internet. The network 1030 in some cases is a telecommunication and/or data network. The network 1030 can include one or more computer servers, which can enable distributed computing, such as cloud computing. The network 1030, in some cases with the aid of the computer system 1001, can implement a peer-to-peer network, which may enable devices coupled to the computer system 1001 to behave as a client or a server.

The CPU 1005 can execute a sequence of machine-readable instructions, which can be embodied in a program or software. The instructions may be stored in a memory location, such as the memory 1010. Examples of operations performed by the CPU 1005 can include fetch, decode, execute, and writeback.

The storage unit 1015 can store files, such as drivers, libraries and saved programs. The storage unit 1015 can store user data, e.g., user preferences and user programs. The computer system 1001 in some cases can include one or more additional data storage units that are external to the computer system 1001, such as located on a remote server that is in communication with the computer system 1001 through an intranet or the Internet.

The computer system 1001 can communicate with one or more remote computer systems through the network 1030. For instance, the computer system 1001 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1001 via the network 1030.

Methods as described herein can be implemented by way of machine (e.g., computer processor) executable code stored on an electronic storage location of the computer system 1001, such as, for example, on the memory 1010 or electronic storage unit 1015. The machine executable or machine readable code can be provided in the form of software. During use, the code can be executed by the processor 1005. In some cases, the code can be retrieved from the storage unit 1015 and stored on the memory 1010 for ready access by the processor 1005. In some situations, the electronic storage unit 1015 can be precluded, and machine-executable instructions are stored on memory 1010.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1001 can include or be in communication with an electronic display that comprises a user interface (UI) for providing, for example, sorted data can be displayed to a user. Examples of UI's include, without limitation, a graphical user interface (GUI) and web-based user interface.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents

What is claimed is:

1. A system for processing a plurality of string data values generated from a nucleic acid sequencing machine upon processing a nucleic acid sample, said system comprising:
a database comprising said plurality of string data values generated from said nucleic acid sequencing machine upon processing said nucleic acid sample; and
one or more computer processors operatively coupled to said database, wherein said one or more computer processors are individually or collectively programmed to:
(i) obtain a string data value from said plurality of string data values;
(ii) map said string data value to a data container among a plurality of data containers, wherein each of said plurality of string data values is addressable by genomic position with respect to a genome;
(iii) append said string data value to said data container
(iv) repeat (i)-(iii) for a remainder of said plurality of string data values; and
(v) output a continuous output sequence generated from (i)-(iv) wherein (i)-(iii) are performed without sorting said plurality of string data values.

2. The system of claim 1, wherein, in (ii), said one or more computer processors are individually or collectively programmed to apply a mapping function to said string data value to obtain a position value associated with said string data value.

3. The system of claim 2, wherein said one or more computer processors are individually or collectively further programmed to select said data container based upon said position value.

4. The system of claim 1, wherein said one or more computer processors are individually or collectively further programmed to:
(i) apply a non-deterministic mapping function to said string data value to obtain (a) a plurality of position values for at least two data containers from said plurality of data containers, and (b) a plurality of probability values each associated with said string data value and with said at least two data containers;
(ii) select said at least two data containers based upon said plurality of position values; and
(iii) append a copy of said string data value, a position value of said plurality of position values, and a probability value of said plurality of probability values to each of said at least two data containers.

5. The system of claim 1, wherein said one or more computer processors are individually or collectively further programmed to (i) generate an output data set by traversing said plurality of data containers in linear order, and (ii) successively output string data value from said plurality of string data values in said plurality of data containers.

6. The system of claim 1, wherein said one or more computer processors are individually or collectively further programmed to:
(i) create a compact data container;
(ii) address said data container;
(iii) copy said string data value in said data container to said compact data container;
(iv) repeat (ii) and (iii) for each of said plurality of string data values in said plurality of data containers to yield a compacted continuous output sequence; and
(v) output said compacted continuous output sequence.

7. The system of claim 1, wherein said one or more computer processors are individually or collectively further programmed to associate a probability value to said string data value mapped to said data container.

8. The system of claim 1, wherein, in (ii), said one or more computer processors are individually or collectively programmed to apply a non-injective mapping function.

9. A non-transitory computer-readable medium comprising machine-executable code that, upon execution by a processor, implements a method for data processing, comprising:
(a) obtaining a string data value from a plurality of string data values;
(b) mapping said string data value to a data container among a plurality of data containers, wherein each of said plurality of string data values is addressable by genomic position with respect to a genome;
(c) appending said string data value to said data container
(d) repeating (a)-(c) for a remainder of said plurality of string data values; and
(e) outputting a continuous output sequence generated from (a)-(d), based on traversing the data containers in (b),
wherein (a)-(c) are performed without sorting said plurality of string data values.

10. The non-transitory computer-readable medium of claim 9, wherein, in (b), said mapping comprises applying a mapping function to said string data value to obtain a position value associated with said string data value.

11. The non-transitory computer-readable medium of claim 10, further comprising selecting said data container based upon said position value.

12. The non-transitory computer-readable medium of claim 9, further comprising:
(a) applying a non-deterministic mapping function to said string data value to obtain (i) a plurality of position values for at least two data containers from said plurality of data containers, and (ii) a plurality of probability values each associated with said string data value and with said at least two data containers;
(b) selecting said at least two data containers based upon said plurality of position values; and
(c) appending a copy of said string data value, a position value of said plurality of position values, and a probability value of said plurality of probability values to each of said at least two data containers.

13. The non-transitory computer-readable medium of claim 9, further comprising (a) generating an output data set by traversing said plurality of data containers in linear order, and (b) successively outputting string data value from said plurality of string data values in said plurality of data containers.

14. The non-transitory computer-readable medium of claim 9, further comprising:
(a) creating a compact data container;
(b) addressing said data container;
(c) copying said string data value in said data container to said compact data container;
(d) repeating (b) and (c) for each of said plurality of string data values in said plurality of data containers to yield a compacted continuous output sequence; and
(e) outputting said compacted continuous output sequence.

15. The non-transitory computer-readable medium of claim 9, further comprising associating a probability value to said string data value mapped to said data container.

16. The non-transitory computer-readable medium of claim 9, wherein, in (b), said mapping comprises applying a non-injective mapping function.

\* \* \* \* \*